(12) United States Patent
Lu

(10) Patent No.: US 9,080,217 B2
(45) Date of Patent: Jul. 14, 2015

(54) METHODS FOR DETECTION OF CLOSTRIDIUM DIFFICILE

(71) Applicant: Roche Molecular Systems, Inc., Pleasanton, CA (US)

(72) Inventor: Shi-Da Y. Lu, San Jose, CA (US)

(73) Assignee: ROCHE MOLECULAR SYSTEMS, INC., Pleasanton, CA (US)

( * ) Notice: Subject to any disclaimer, the term of this patent is extended or adjusted under 35 U.S.C. 154(b) by 112 days.

(21) Appl. No.: 13/624,032

(22) Filed: Sep. 21, 2012

(65) Prior Publication Data

US 2014/0087371 A1    Mar. 27, 2014

(51) Int. Cl.
*C12Q 1/68* (2006.01)
*C07H 21/04* (2006.01)

(52) U.S. Cl.
CPC ..................................... *C12Q 1/689* (2013.01)

(58) Field of Classification Search
None
See application file for complete search history.

(56) References Cited

U.S. PATENT DOCUMENTS

| 8,101,362 B2 | 1/2012 | Cockerill, III et al. |
| 2009/0208948 A1* | 8/2009 | Paquette et al. ................... 435/6 |

FOREIGN PATENT DOCUMENTS

| WO | 2010062897 A1 | 6/2010 |
| WO | 2011008942 A2 | 1/2011 |
| WO | PCTEP2013069556 | 10/2013 |

OTHER PUBLICATIONS

Drudy, Denise, et al., 2007, "Toxin A-negative, toxin B-positive *Clostridium difficile*", International Journal of Infectious Diseases, 11:5-10.
Green, Gaynor A., et al., 1995, "Cloning and characterization of the cytotoxin L-encoding gene of *Clostridium sordellii*: homology with *Clostridium difficile* cytotoxin B", Gene, 161:57-61.
Green, G. A., et al., 1996, "Characterisation of an enterotoxin-negative cytotoxin-positive strain of *Clostridium sordellii*", J. Med. Microbiology, 44:60-64.
Guilbault, C., et al., 2002, "Development and Evaluation of a PCR Method for Detection of the *Clostridium difficile* Toxin B Gene in Stool Specimens", Journal of Clinical Microbiology, 40(6):2288-2290.
Database Geneseq [online], 2011, "*Clostridium difficile* cdtB gene specific probe, SEQ ID 2128" retrieved from EBI accession No. GSN:AYM81421 Database accession No. AYM81421.
Lyras, Dena, et al., 2009, "Toxin B is essential for virulence of *Clostridium difficile*", Nature, 458:1176-1179.
Peterson, Lance R., et al., 2007, "Detection of Toxigenic *Clostricium difficile* in Stool Samples by Real-Time Polymerase Chain Reaction for the Diagnosis of *C. difficile*—Associated Diarrhea", Clinical Infectious Diseases, 45 (9):1152-1160.
Van Den Berg, R. J., et al, 2006, "Rapid diagnosis of toxinogenic *Clostridium difficile* in faecal samples with internally controlled real-time PCR", Clinical Microbiology and Infection, 12(2):184-186.

* cited by examiner

*Primary Examiner* — Diana B Johannsen
(74) *Attorney, Agent, or Firm* — M. Reza Savari

(57) ABSTRACT

Methods for the rapid detection of the presence or absence of *Clostridium difficile* in a biological or nonbiological sample are described. The methods can include performing an amplifying step, a hybridizing step, and a detecting step. Furthermore, primers, probes, and kits are provided that are designed for the detection of *Clostridium difficile*.

4 Claims, 2 Drawing Sheets

METHODS FOR DETECTION OF CLOSTRIDIUM DIFFICILE

FIELD OF THE INVENTION

The present invention relates to the field of microbial diagnostic, and more particularly, to detection of *Clostridium difficile*.

BACKGROUND OF THE INVENTION

*Clostridium difficile* ("*C. difficile*" or "*C. diff*") is an anaerobic, Gram-positive, spore-forming bacteria that can causes severe diarrhea and other intestinal disease. *C. difficile* spores are frequently found in hospitals, and although spores cannot cause infection directly, they can transform into the active infectious form when ingested. *C. difficile* infections include a wide range of clinical syndromes from simple diarrhea to pseudomembranous colitis associated with significant morbidity and mortality. Antibiotic-associated colitis is an infection of the colon caused by *C. difficile* that occurs when competing bacteria in the gut flora have been wiped out by antibiotics. It is the most common infection acquired by patients while they are in the hospital.

The majority of infections with *C. difficile* occur among persons aged 65 years or older and among patients in healthcare facilities, such as hospitals and nursing homes. From 1996 to 2009, *C. difficile* rates for hospitalized persons aged 65 years or older increased 200%, with increases of 175% for those aged 65-74 years, 198% for those aged 75-84 years, and 201% for those aged 85 years or older. *C. difficile* rates among patients aged 85 years or older were notably higher than those for the other age groups (National Hospital Discharge Survey, Annual Files, 1996-2009).

Diagnosing *C. difficile* colitis commonly involves a test that detects toxins produced by *C. difficile* in a stool sample. There are two different *C. difficile* toxins that are capable of causing colitis, referred to as toxin A (tdcA) and toxin B (tcdB). Diagnostic tests for these toxins are available commercially. However, these tests are not perfect and can result in false positive tests (finding toxins when there is no *C. difficile*) and false negative tests (not finding toxins when *C. difficile* is present) can occur. For example, the possibility of a cross-reaction between *C. difficile* and *C. sordellii* is known. See, "Cloning and characterization of the cytotoxin L-encoding gene of *Clostridium sordellii*: homology with *Clostridium difficile* cytotoxin B", Green et. al., Gene, 1995, 161:57-61). Thus, there is still a significant clinical need to develop molecular testing for detection of *C. difficile* that is more sensitive than culture and less susceptible to false positive or false negative results.

SUMMARY OF THE INVENTION

Embodiments of the present invention relates to methods for the rapid detection of the presence or absence of *C. difficile* in a biological or nonbiological sample. The present invention includes methods of detection of *C. difficile* comprising performing at least one cycling step, which may include an amplifying step and a hybridizing step. Furthermore, the present invention relates to primers, probes, and kits that are designed for the detection of *C. difficile*. The gene targeted in the methods of the present invention for the detection of *C. difficile* is the *C. difficile* toxin B (tcdB) gene. For example, the tcdB gene encoding cytotoxin B was chosen because it was determined to be specific to toxigenic *C. difficile* and not present in other *Clostridium* species, with the exception of some enterotoxin-negative, cytotoxin-positive strains of *Clostridium sordellii* (Green, et. al., J. Med. Microbiol. 1996, 44:60-64). The heterogenity of the tcdB gene among toxigenic *C. difficile* strains results in up to 31 toxinotypes thus far including Tox 0 which is the reference strain VPI 10463. The tcdB gene encodes a single-stranded protein having a C-terminal domain responsible for binding to the host cell membrane, a middle part involved in internalization, and the N-terminal catalytic (toxic) part (Rupnik, et al., Microbiology, 2005, 151(1):199-208).

In one aspect, the present invention provides an oligonucleotide comprising or consisting of a sequence of nucleotides selected from SEQ ID NOs: 1, 2, 3, 4, 5, 6, 7, 8, and 9 or a complement thereof, which oligonucleotide has 100 or fewer nucleotides. In another aspect, the present invention provides an oligonucleotide that includes a nucleic acid having at least 70% sequence identity (e.g., at least 75%, 80%, 85%, 90% or 95%, etc.) to one of SEQ ID NOs: 1, 2, 3, 4, 5, 6, 7, 8, and 9, or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g., 35 or fewer nucleotides, 30 or fewer nucleotides, etc.). In some embodiments, the oligonucleotides comprise at least one modified nucleotide, e.g., to alter nucleic acid hybridization stability relative to unmodified nucleotides. Optionally, the oligonucleotides comprise at least one label and/or at least one quencher moiety. In some embodiments, the oligonucleotides include at least one conservatively modified variation.

In a further aspect, the present invention provides a method for detecting in a sample, the method comprising performing an amplifying step comprising contacting the sample with a set of tcdB primers to produce an amplification product if *C. difficile* is present in the sample; performing a hybridizing step comprising contacting the amplification product with one or more detectable tcdB probes; and detecting the presence or absence of the amplified product, wherein the presence of the amplified product is indicative of the presence of *C. difficile* in the sample and wherein the absence of the amplified product is indicative of the absence of *C. difficile* in the sample. In one embodiment, each primer of the set of tcdB primers comprises or consists of a sequence of nucleotides selected from the group consisting of SEQ ID NOs: 1, 2, 3, 4, 5, and 6, or a complement thereof; and wherein the one or more detectable tcdB probes comprise or consists of a sequence of nucleotides selected from the group consisting SEQ ID NOs: 7, 8, and 9, or a complement thereof. In some embodiments, a hybridizing step includes contacting the amplification product with a probe that is labeled with a donor fluorescent moiety and a corresponding acceptor fluorescent moiety. The method further includes detecting the presence or absence of fluorescence resonance energy transfer (FRET) between the donor fluorescent moiety and the acceptor fluorescent moiety of the probe. The presence or absence of fluorescence is indicative of the presence or absence of *C. difficile* in the sample.

In one aspect, amplification can employ a polymerase enzyme having 5' to 3' exonuclease activity. Thus, the first and second fluorescent moieties may be within no more than 5 nucleotides of each other along the length of the probe. In another aspect, the tcdB probe includes a nucleic acid sequence that permits secondary structure formation. Such secondary structure formation generally results in spatial proximity between the first and second fluorescent moiety. According to this method, the second fluorescent moiety on the probe can be a quencher.

In still another aspect, the invention provides for methods of detecting the presence or absence of C. difficile in a biological sample from an individual. Such methods generally include performing at least one cycling step, which includes an amplifying step and a dye-binding step. Typically, the amplifying step includes contacting the sample with a pair of tcdB primers to produce a tcdB amplification product if a tcdB nucleic acid molecule is present in the sample and the dye-binding step includes contacting the tcdB amplification product with a double-stranded DNA binding dye. Such methods also include detecting the presence or absence of binding of the double-stranded DNA binding dye into the amplification product, wherein the presence of binding is indicative of the presence of C. difficile in the sample, and wherein the absence of binding is indicative of the absence of C. difficile in the sample. A representative double-stranded DNA binding dye is ethidium bromide. In addition, such methods also can include determining the melting temperature between the tcdB amplification product and the double-stranded DNA binding dye, wherein the melting temperature confirms the presence or absence of the C. difficile.

In a further aspect, the present invention provides a kit for detecting a nucleic acid of C. difficile (tcdB target). The kit can include a first oligonucleotide comprising or consisting of a sequence selected from the group consisting of SEQ ID NOs: 1, 2, and 3, or a complement thereof; a second oligonucleotide comprising or consisting of a sequence selected from the group consisting of SEQ ID NOs: 4, 5, and 6, or a complement thereof; and a third detectably labeled oligonucleotide comprising or consisting of a sequence selected from the group consisting of SEQ ID NOs: 7, 8, and 9, or a complement thereof.

In one aspect, the kit can include probes already labeled with donor and corresponding acceptor fluorescent moieties, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of C. difficile in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIGS. 1A, 1B, and 1C show gel data of PCR products produced with various primer pairs for toxin B gene of C. Difficile and the level of cross reactivity with C. sordellii; CDB203BZ/CDB202BZ (FIG. 1A), CDN211BZ/CDB214N (FIG. 1B), and CDB205BZ/CDB204BZ (FIG. 1C).

FIGS. 2A, 2B, and 2C show PCR growth curves of the CDB242HQ6 probe in amplification of genomic DNA of C. difficile Tox 0 and C. sordellii with various primer pairs: CDB203BZ/CDB202BZ (FIG. 2A), CDN211BZ/CDB214N (FIG. 2B), and CDB205BZ/CDB204BZ (FIG. 2C).

DETAILED DESCRIPTION OF THE INVENTION

A real-time assay for detecting C. difficile in a sample is described herein. Primers and probes for detecting C. difficile are provided, as are articles of manufacture or kits containing such primers and probes. The increased sensitivity of real-time PCR for detection of C. difficile compared to other methods, as well as the improved features of real-time PCR including sample containment and real-time detection of the amplified product, make feasible the implementation of this technology for routine diagnosis of C. difficile infections in the clinical laboratory.

The methods may include performing at least one cycling step that includes amplifying a portion of a tcdB nucleic acid molecule from a sample using a pair of tcdB primers. "tcdB primers" as used herein refers to oligonucleotide primers that specifically anneal to nucleic acid sequences encoding tcdB and initiate synthesis therefrom under appropriate conditions. Each of the tcdB primers anneals to a target within or adjacent to a tcdB nucleic acid molecule such that at least a portion of each amplification product contains nucleic acid sequence corresponding to tcdB. The tcdB amplification product is produced provided that tcdB nucleic acid is present in the sample, thus the presence of the tcdB amplification product is indicative of the presence of C. difficile in the sample. The amplification product should contain the nucleic acid sequences that are complementary to one or more detectable tcdB probes. Each cycling step includes an amplification step, a hybridization step, and a detection step, in which the sample is contacted with the one or more detectable tcdB probes for detection of the presence or absence of C. difficile in the sample.

As used herein, the term "amplifying" refers to the process of synthesizing nucleic acid molecules that are complementary to one or both strands of a template nucleic acid molecule (e.g., tcdB nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" is used herein as known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe" according to the invention.

The term "hybridizing" refers to the annealing of one or more probes to an amplification product. Hybridization conditions typically include a temperature that is below the melting temperature of the probes but that avoids non-specific hybridization of the probes.

The term "5' to 3' exonuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus*, *T. ruber*, *T. thermophilus*, *T. aquaticus*, *T. lacteus*, *T. rubens*, *Bacillus stearothermophilus*, and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl Ribo-U, 2'-0-methyl Ribo-C, an N4-ethyl-dC, an N6-methyl-dA, and the like. Many other modified nucleotides that can be substituted in the oligonucleotides of the invention are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments of the invention. Examples of these types of nucleic acid modifications are described in, e.g., U.S. Pat. No. 6,001,611, which is incorporated herein by reference.

C. difficile Nucleic Acids and Oligonucleotides

The invention provides methods to detect *C. difficile* by amplifying, for example, a portion of the tcdB gene. Nucleic acid sequences of tcdB gene from *C. difficile* are available (see, for example, GenBank Accession No. AM180355. Specifically, primers and probes to amplify and detect tcdB nucleic acid molecules are provided by the present invention.

For detection of *C. difficile*, primers and probes to amplify tcdB nucleic acid molecules are provided. TcdB nucleic acids other than those exemplified herein can also be used to detect *C. difficile* in a sample. For example, functional variants can be evaluated for specificity and/or sensitivity by those of skill in the art using routine methods. Representative functional variants can include, e.g., one or more deletions, insertions, and/or substitutions in the tcdB nucleic acids disclosed herein.

More specifically, the oligonucleotides of the present invention each include a nucleic acid with a sequence selected from SEQ ID NOs: 1, 2, 3, 4, 5, 6, 7, 8, and 9, a substantially identical variant thereof in which the variant has at least, e.g., 80%, 90%, or 95% sequence identity to one of SEQ ID NOs: 1, 2, 3, 4, 5, 6, 7, 8, and 9, or a complement of SEQ ID NOs: 1, 2, 3, 4, 5, 6, 7, 8, and 9 and the variant.

TABLE I

Forward Primers

| SEQ ID NO | SEQUENCE |
|---|---|
| 1 | 5'-ATAAAGAAACTGGAGAATCTATA-3' |
| 2 | 5'-GAAACTGGAGAATCTATATTTGTA-3' |
| 3 | 5'-CTGGAGAATCTATATTTGTAGAAAC-3' |

TABLE II

Reverse Primers

| SEQ ID NO | SEQUENCE |
|---|---|
| 4 | 5'-TAATGATTGTATAAAAAATGCAGC-3' |
| 5 | 5'-CTTAAATTACTAAGAGATTCTTTAGAAC-3' |
| 6 | 5'-CTTAAATTACTAAGAGATTCTTTAGAA-3' |

TABLE III

Probes

| SEQ ID NO | SEQUENCE |
|---|---|
| 7 | 5'-TACTGTAAATGGTAAGTTAGTAAAAAAAGT-3' |
| 8 | 5'-TACTGTAAATGGTAAGTTGGTAAAAAAAGT-3' |
| 9 | 5'-AACTTACCATTTACAGTATCAAATATAGTA-3' |

In one embodiment of the invention, a particular set of tcdB primers and probe is used in order to provide for detection of

*C. difficile* in a biological sample suspected of containing *C. difficile*. The set of primers and probe may comprise at least one primer and probe specific for tcdB comprising or consisting of a nucleic acid sequence selected from the group consisting of SEQ ID NOs: 1, 2, 3, 4, 5, 6, 7, 8, and 9. In another embodiment of the invention, the primer and for tcdB comprises or consists of a functionally active variant of any of the primers of SEQ ID NOs: 1, 2, 3, 4, 5, 6, 7, 8, and 9.

A functionally active variant of any of the primers and/or probes of SEQ ID NOs: 1, 2, 3, 4, 5, 6, 7, 8, and 9 may be identified by using the primers and/or probes in the method of the invention. A functionally active variant of a primer and/or probe of any of the SEQ ID NOs: 1, 2, 3, 4, 5, 6, 7, 8, and 9 pertains to a primer which provides a similar or higher specificity and sensitivity in the method or kit of the invention as compared to the respective sequence of SEQ ID NOs: 1, 2, 3, 4, 5, 6, 7, 8, and 9.

The variant may, e.g., vary from the sequence of SEQ ID NOs: 1, 2, 3, 4, 5, 6, 7, 8, and 9 by one or more nucleotide additions, deletions or substitutions such as one or more nucleotide additions, deletions or substitutions at the 5' end and/or the 3' end of the respective sequence of SEQ ID NOs: 1, 2, 3, 4, 5, 6, 7, 8, and 9. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding tcdB, e.g., nucleic acids encoding alternative portions of tcdB, can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods of the invention may use one or more probes in order to detect the presence or absence of *C. difficile*. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a tcdB (target) nucleic acid. A "probe" can be referred to as a "detection probe" meaning that it detects the target nucleic acid.

According to the invention, the tcdB probe can be labeled with at least one fluorescent label. In one embodiment, the tcdB probe can be labeled with a donor fluorescent moiety, e.g., a fluorescent dye, and a corresponding acceptor fluorescent moiety, e.g., a quencher.

In one embodiment of the present invention, at least one probe comprises or consists of a fluorescent moiety and a nucleic acid sequences selected from the group consisting of SEQ ID NOs: 7, 8, and 9 (shown without the label).

Designing oligonucleotides to be used as hybridization probes can be performed in a manner similar to the design of primers. Embodiments of the present invention may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 30 (e.g., 16, 18, 20, 21, 22, 23, 24, or 25) nucleotides in length.

Constructs of the present invention include vectors containing a tcdB nucleic acid molecule (e.g., SEQ ID NOs: 1, 2, 3, 4, 5, 6, 7, 8, and 9). Constructs of the invention can be used, for example, as control template nucleic acid molecules. Vectors suitable for use in the present invention are commercially available and/or produced by recombinant nucleic acid technology methods routine in the art. TcdB nucleic acid molecules can be obtained, for example, by chemical synthesis, direct cloning from *C. difficile* or by PCR amplification.

Constructs suitable for use in the methods of the invention typically include, in addition to tcdB nucleic acid molecules (e.g., a nucleic acid molecule that contains one or more sequences of SEQ ID NOs: 1, 2, 3, 4, 5, 6, 7, 8, and 9), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing tcdB nucleic acid molecules can be propagated in a host cell. As used herein, the term host cell is meant to include prokaryotes and eukaryotes such as yeast, plant and animal cells. Prokaryotic hosts may include *E. coli*, *Salmonella typhimurium*, *Serratia marcescens*, and *Bacillus subtilis*. Eukaryotic hosts include yeasts such as *S. cerevisiae*, *S. pornbe*, *Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotides capable of acting as a point of initiation of nucleic acid synthesis within tcdB nucleic acid sequences (e.g., SEQ ID NOs: 1, 2, 3, 4, 5, and 6). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the tcdB nucleic acid. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ *C. difficile* nucleic acid such as RNA or DNA (cDNA). The template nucleic acid need not be purified; it may be a minor fraction of a complex mixture, such as *C. difficile* nucleic acid contained in human cells. *C. difficile* nucleic acids may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs: 1, 2, 3, 4, 5, and 6) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target tcdB nucleic acid molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength.

In one example, a oligonucleotide probe can contain a donor fluorescent moiety and a corresponding quencher, which dissipates the transferred energy in a form other than light. When the probe is intact, energy transfer typically occurs between the two fluorescent moieties such that fluorescent emission from the donor fluorescent moiety is quenched. During an extension step of a polymerase chain reaction, a probe bound to an amplification product is cleaved by the 5' to 3' exonuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the tcdB target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm for the purpose of the present invention is the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety such as an LC Red 640-NHS-ester can be combined with C6-Phosphoramidites (available from ABI (Foster City, Calif.) or Glen Research (Sterling, Va.)) to produce, for example, LC Red 640-Phosphoramidite. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPGs that require coupling of a fluorescein-NHS-ester after oligonucleotide synthesis.

Detection of *Clostridium difficile*

The present invention provides methods for detecting the presence or absence of *C. difficile* in a biological or non-biolobical sample. The claimed methods can avoid problems of sample contamination, e.g., carry-over contamination from run to run, false negatives, e.g., sensitivity, and false positives, e.g., specificity. The methods include performing at least one cycling step that includes amplifying a portion of a tcdB nucleic acid molecule from a sample using a pair of tcdB primers, and a FRET detecting step. Multiple cycling steps are performed, preferably in a thermocycler. Methods of the invention can be performed using the tcdB primers and probes to detect the presence of tcdB, and the detection of tcdB indicates the presence of a *C. difficile* in the sample.

As described herein, amplification products can be detected using labeled hybridization probes that take advantage of FRET technology. One FRET format utilizes TaqMan® technology to detect the presence or absence of an amplification product, and hence, the presence or absence of *C. difficile*. TaqMan® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TaqMan® technology, and is suitable for performing the methods described herein for detecting the presence or absence of *C. difficile* in the sample.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of C. difficile genomes). If amplification of tcdB nucleic acid occurs and an amplification product is produced, the step of hybridizing results in a detectable signal based upon FRET between the members of the pair of probes.

Generally, the presence of FRET indicates the presence of C. difficile in the sample, and the absence of FRET indicates the absence of C. difficile in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of a C. difficile infection.

Representative biological samples that can be used in practicing the methods of the invention include, but are not limited to dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release C. difficile nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the tcdB probes from the tcdB amplification product can confirm the presence or absence of C. difficile in the sample.

Within each thermocycler run, control samples are cycled as well. Positive control samples can amplify C. difficile nucleic acid control template (other than tcdB) using, for example, control primers and control probes. Positive control samples can also amplify, for example, a plasmid construct containing tcdB nucleic acid molecules. Such a plasmid control can be amplified internally (e.g., within the sample) or in a separate sample run side-by-side with the patients' samples. Each thermocycler run can also include a negative control that, for example, lacks C. difficile template DNA. Such controls are indicators of the success or failure of the amplification, hybridization, and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods of the invention. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

It is understood that the present invention is not limited by the configuration of one or more commercially available instruments.

Articles of Manufacture/Kits

The present invention further provides for articles of manufacture or kits to detect C. difficile. An article of manufacture according to the present invention can include primers and probes used to detect C. difficile, together with suitable packaging materials. Representative primers and probes for detection of C. difficile are capable of hybridizing to tcdB nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to tcdB nucleic acid molecules are provided.

Articles of manufacture of the invention can also include one or more fluorescent moieties for labeling the probes or, alternatively, the probes supplied with the kit can be labeled. For example, an article of manufacture may include a donor fluorescent moiety for labeling one of the tcdB probes and an acceptor fluorescent moiety for labeling the other tcdB probe, respectively. Examples of suitable FRET donor fluorescent moieties and corresponding acceptor fluorescent moieties are provided above.

Articles of manufacture of the invention can also contain a package insert or package label having instructions thereon for using the tcdB primers and probes to detect C. difficile in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

The following examples and figures are provided to aid the understanding of the present invention, the true scope of which is set forth in the appended claims. It is understood that modifications can be made in the procedures set forth without departing from the spirit of the invention.

Example 1

Cross-Reactivity with *C. sordellii*

Three activated master mix (MMx) comprised the following primer sets: a) CDB203BZ/CDB202BZ (alkylated versions of SEQ ID NOs: 2 and 4—both primer are (benzyl) alkylated at the 3' terminal base, b) CDB211BZ/CDB214N, the forward primer is (benzyl) alkylated and the reverse primer is not alkylated, and c) CDB205BZ/CDB204BZ (alkylated versions of SEQ ID NOs: 3 and 5—both primers are (benzyl) alkylated at the 3' terminal base were tested using the same probe CDB242HQ6 (SEQ ID NO. 9) which is a naked probe for detection.

Figures 1A, 1B, 1C, 2A:
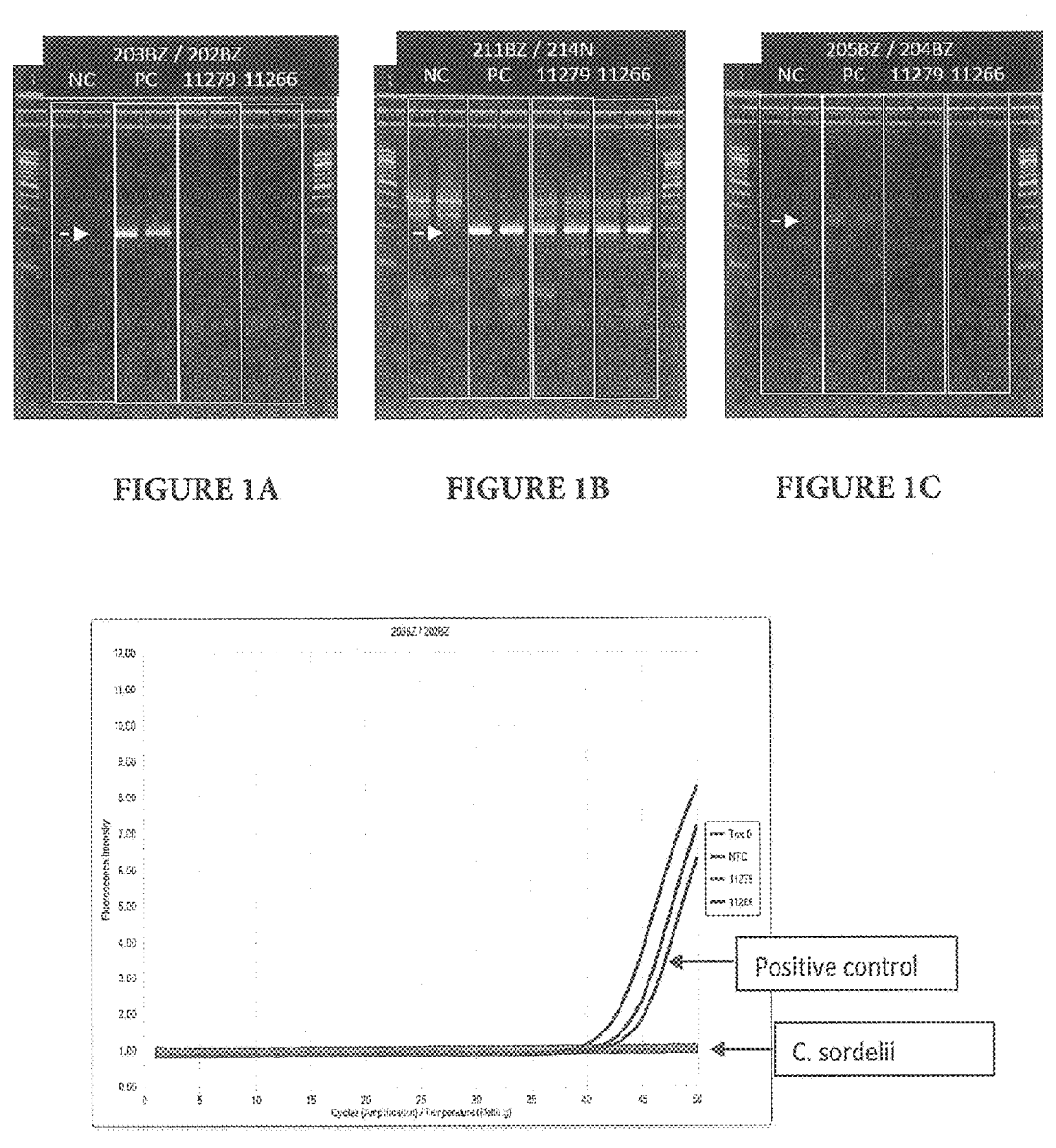

Genomic DNA templates of Tox 0 at 1+E3 genomic equivalent (ge) input in triplicates and exclusivity species of *C. sordellii* 11279 and 11266 at 1+E6 ge input in 6 replicates, along with no template control buffer were amplified with the 3 activated MMx's on an LC480 Instrument. Replicate reactions for each template were run on gel along with the 100 bp molecular weight marker (FIGS. 1A-C).

The gel data showed the most specific PCR product was generated from CDB211BZ/124N, followed by CDB203BZ/202BZ, and then CDB205BZ/204BZ for the positive control template; the negative controls did not reveal any PCR specific product with all 3 primer sets, but non-specific product was a phenomenon for primer pair CDB211BZ/214N. Of the three primer pairs, only CDB211BZ/214N generated visible specific PCR products using the two *C. sordellii* isolates 11279 and 11266 as the template. On occasion, CDB203BZ/202BZ would generate PCR specific product against genomic template of *C. sordellii*, however the product yield never matched up with CDB211BZ/214N. (NC: No template control, PC: *C. diff* Tox 0 genomic DNA, 100 bp ladder as the molecular weight marker.)

Figures 2B, 2C:
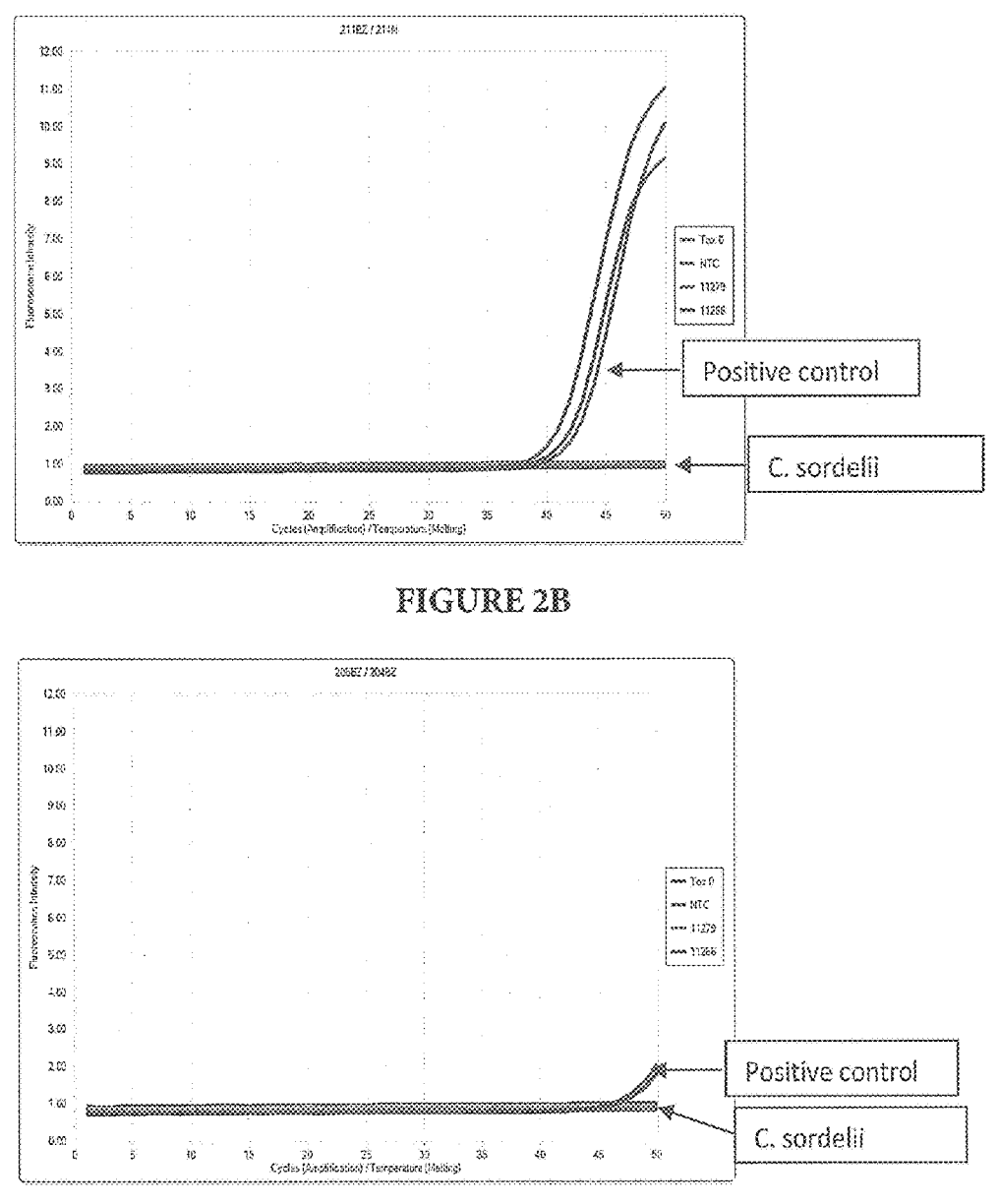

Although amplification of *C. sordellii* was occurring with primer pair CDB211BZ/214N (FIG. 1B), the probe however, was capable of discriminating against *C. sordelii* without generating any growth curves (FIG. 2B).

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A method of detecting *C. difficile* in a sample, the method comprising:

performing an amplifying step comprising contacting the sample with a set of tcdB primers to produce an amplification product if a tcdB nucleic acid is present in the sample;

performing a hybridizing step comprising contacting the sample and the amplification product, if produced, with a detectable tcdB probe; and detecting the presence or absence of the amplification product, wherein the presence of the amplification product is indicative of the presence of *C. difficile* in the sample and wherein the absence of the amplification product is indicative of the absence of *C. difficile* in the sample;

wherein the set of tcdB primers comprises a first primer consisting of the sequence of SEQ ID NO: 2 or the complement thereof, and a second primer consisting of the sequence of SEQ ID NO: 4 or the complement thereof;

wherein the detectable tcdB probe comprises an oligonucleotide consisting of the sequence of SEQ ID NO: 9 or the complement thereof, and wherein the detectable tcdB probe is labeled with a donor fluorescent moiety and a corresponding acceptor moiety; and wherein the detecting comprises detecting the presence or absence of fluorescence resonance energy transfer (FRET) between the donor fluorescent moiety and the acceptor moiety of the probe, wherein the presence or absence of fluorescence is indicative of the presence or absence of *C. difficile* in the sample.

2. The method of claim 1, wherein said amplifying step employs a polymerase enzyme having 5' to 3' exonuclease activity.

3. The method of claim 2, wherein said donor fluorescent moiety and said acceptor moiety are within no more than 5 nucleotides of each other on said probe.

4. The method of claim 3, wherein said acceptor moiety is a quencher.

* * * * *

SEQUENCE LISTING

```
<160> NUMBER OF SEQ ID NOS: 9

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide

<400> SEQUENCE: 1
ataaagaaac tggagaatct ata                                              23

<210> SEQ ID NO 2
<211> LENGTH: 24
<212> TYPE: DNA
<213> ORGANISM: Artificial Sequence
<220> FEATURE:
<223> OTHER INFORMATION: Oligonucleotide

<400> SEQUENCE: 2
gaaactggag aatctatatt tgta                                             24

<210> SEQ ID NO 3
<211> LENGTH: 25
<212> TYPE: DNA
<213> ORGANISM: Artificial Sequence
<220> FEATURE:
<223> OTHER INFORMATION: Oligonucleotide

<400> SEQUENCE: 3
ctggagaatc tatatttgta gaaac                                            25

<210> SEQ ID NO 4
<211> LENGTH: 24
```

```
<212> TYPE: DNA
<213> ORGANISM: Artificial Sequence
<220> FEATURE:
<223> OTHER INFORMATION: Oligonucleotide

<400> SEQUENCE: 4
taatgattgt ataaaaaatg cagc                                         24

<210> SEQ ID NO 5
<211> LENGTH: 28
<212> TYPE: DNA
<213> ORGANISM: Artificial Sequence
<220> FEATURE:
<223> OTHER INFORMATION: Oligonucleotide

<400> SEQUENCE: 5
cttaaattac taagagattc tttagaac                                     28

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide

<400> SEQUENCE: 6
cttaaattac taagagattc tttagaa                                      27

<210> SEQ ID NO 7
<211> LENGTH: 30
<212> TYPE: DNA
<213> ORGANISM: Artificial Sequence
<220> FEATURE:
<223> OTHER INFORMATION: Oligonucleotide

<400> SEQUENCE: 7
tactgtaaat ggtaagttag taaaaaaagt                                   30

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide

<400> SEQUENCE: 8
tactgtaaat ggtaagttgg taaaaaaagt                                   30

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide

<400> SEQUENCE: 9
aacttaccat ttacagtatc aaatatagta                                   30
```